United States Patent
Markov et al.

(10) Patent No.: US 6,312,707 B1
(45) Date of Patent: Nov. 6, 2001

(54) TREATMENT OF SICKLE CELL ANEMIA CRISES WITH FRUCTOSE-1,6-DIPHOSPHATE AS AN ANALGESIC DRUG

(75) Inventors: Angel K. Markov, Jackson, MS (US); Anthony W. Fox, Rancho LaCosta; Paul J. Marangos, Encinitas, both of CA (US)

(73) Assignee: Questcor Pharmaceuticals, Inc., Union City, CA (US)

( * ) Notice: Subject to any disclaimer, the term of this patent is extended or adjusted under 35 U.S.C. 154(b) by 0 days.

(21) Appl. No.: 09/591,786

(22) Filed: Jun. 12, 2000

Related U.S. Application Data

(63) Continuation of application No. 08/943,688, filed on Oct. 3, 1997, now Pat. No. 6,074,658.

(51) Int. Cl.[7] ............................................ A61F 2/02
(52) U.S. Cl. ................................................ 424/423
(58) Field of Search ........................................... 424/423

(56) References Cited

U.S. PATENT DOCUMENTS

| | | | |
|---|---|---|---|
| 4,530,902 | 7/1985 | Perri et al. | 435/105 |
| 4,546,095 | 10/1985 | Markov | 514/23 |
| 4,703,040 | 10/1987 | Markov | 514/23 |
| 4,870,057 | 9/1989 | Chiapparelli et al. | 514/23 |
| 5,039,665 | 8/1991 | Markov | 514/23 |
| 5,094,947 | 3/1992 | Nakajima et al. | 435/105 |
| 5,434,255 | 7/1995 | Katayama et al. | 536/117 |
| 5,506,210 | 4/1996 | Parish et al. | 514/23 |
| 6,074,658 * | 6/2000 | Markov et al. | 424/423 |

FOREIGN PATENT DOCUMENTS

| | | | |
|---|---|---|---|
| 1089615 | 7/1994 | (CN) | C07H/1/06 |
| 1089616 | 7/1994 | (CN) | C07H/11/04 |
| 1089654 | 7/1994 | (CN) | C12N/1/18 |
| 3323850 | 1/1985 | (DE) | A61K/31/70 |
| 0814087 A | 12/1997 | (EP) . | |

OTHER PUBLICATIONS

Sernov, L.N., et al, "A comparative evaluation of the cardioprotective and antianginal actions of energy–providing agents," *Eksp Klin Farmakol* 55:13–15 (1992) (abstract).

Stryer, L., *Biochemistry*, 2nd ed., pp. 266–267 (Freeman & Co., San Francisco, 1981).

Zhang, J.N., et al, "Protective effect of exogenous fructose–1,6–diphosphate in cardiogenic shock," *Cardiovasc Res* 22: 927–32 (1988).

Lazzarino, G., et al, "Ischemia and reperfusion: effect of fructose–1,6–bisphosphate," *Free Radic Res Commun 16*: 325–39 (1992).

Marchionni, N., et al., "Hemodynamic and electrocardiographic effects of fructose–1,6–diphosphate in acute myocardial infarction," *Am J Cardiol* 56: 266–269 (1985).

Markov, A.K., et al, "Improvement of hemodynamics and pulmonary function following fructose 1–6 diphosphate administration in ARDS patients," *Microcirculation* 1: 173–178 (1987).

(List continued on next page.)

Primary Examiner—Carlos A. Azpuru
(74) Attorney, Agent, or Firm—Pennie & Edmonds LLP

(57) ABSTRACT

Fructose-1,6-diphosphate (FDP) has been shown, in double-blinded controlled clinical trials on patients with sickle cell anemia, to substantially reduce the pain suffered by such patients during the recurrent ischemic crises that are caused by red blood cell sickling. Tests on patients who have been hospitalized for such crises demonstrated that when they received an intravenous injection of FDP, they reported substantially lower pain levels during their hospital stays than control groups that received identical treatment without any FDP. Apparently, FDP has never previously been used or even tested in human clinical trials, to treat sickle cell anemia. In addition, FDP has never previously been reported to have any analgesic (pain-reducing) activity.

9 Claims, 5 Drawing Sheets

OTHER PUBLICATIONS

Markov, A.K., et al "Hemodynamic electrocardiographic, and metabolic effects of fructose diphosphate on acute myocardial ischemia," *Am Heart J 100*: 639–46 (1980).

Markov, A.K., "Hemodynamics and metabolic effects of fructose 1–6 diphosphate in ischemia and shock—experimental and clinical observations," *Ann Emerg Med 15*: 1470–7 (1986).

Markov, A.K., et al, "Increasing survival of dogs subjected to hemorrhagic shock by administration of fructose 1–6 diphosphate," *Surgery 102* : 515–27 (1987).

Pasque, M.K., et a, "Metabolic intervention to affect myocardial recovery following ischemia," *Annals of Surgery 200*: 1–12 (1984).

Sernov, L.N., et al, "The characteristics of the cardioprotective action of fructose–1,6–diphosphate," *Biull Eksp Biol Med 111*:172–3 (1991) (abstract).

Sernov, L.N., et al, "The antiacidotic and cardio–protective effects of fructose–1,6–diphosphate and dehydroascorbic acid," *Farmakol Toksikol 54*:24–26 (1991) (abstract).

Angelos, M.G., et al, "Fructose–1,6–diphosphate fails to limit early myocardial infarction size in a canine model," *Ann. Emerg. Med. 22*: 171–177 (1993).

Brunswick, R., et al, "Preservation of myocardium by infusion of fructose diphosphate following coronary occlusion," *Am J Cardiol 49*: 1008 (1982).

Cargnoni, A., et al, "Role of timing of administration in the cardioprotective effect of fructose–1,6–bisphosphate," *Cardiovasc Drugs Ther 6*: 209–17 (1992).

Colomer, D., et al, "Erythrocyte fructose 2,6–bisphosphate content in congenital hemolytic anemias" (abstract), *Hemoglobin 15*: 517–23 (1991).

Conti, V.R., et al, "Metabolic and functional effects of carbohydrate substrate with single–dose and multiple–dose potassium cardioplegia," *Ann. Thoracic Surg. 36*: 320–327 (1983).

Eddy, L.J., et al, "Lack of a direct metabolic effect of fructose, 1,6–diphosphate in ischemic myocardium," *Am J Physiol 241*: H576–83 (1995).

"Esafosfina" sales brochure (Biomedica Foscama; Ferentino, Italy.

Farias, L.A., et al, "Effects of fructose–1,6–diphosphate, glucose and saline on cardiac resuscitation," *Anesthesiology 65*: 595–601 (1986).

Granot, H., et al, "Successful treatment of irreversible hemorrhagic shock in dogs with fructose–1,6 diphosphate and dichloroacetate," *Circ Shock* 163–73 (1985).

Hassinen, I.E., et al, "Mechanism of the effect of exogenous FDP on myocardial energy metabolism," *Circulation 83*: 584–593 (1991).

Lazzarino G., et al, "Protective effects of exogenously administered fructose–1,6–diphosphate from ischemia reperfusion damage induced on isolated rat heart," *Ital J Biochem 38*: 251A–253A (1989).

Berkow et al., "The Merck Manual of Diagnosis and Therapy."(1987) p. 1120–1121 (paragraph 4) Merck Sharp & Dohme Research Laboratories.

Didlake R. et al., "Prevention of Ischemic Renal Failure with Fructose–1, 6–Dl Phosphate." (Jan. 1984) Annual meeting of the Southern Society for Clinical Investigation, New Orleans, LA.

Farias, L.A. et al., "Prevention of ischemic–hypoxic brain injury and death in rabbits with fructose–1, 6–diphosphate", 1990, 21(4), 606–13 Stroke (Dallas); Coden: SJCCA7; ISSN: 0039–2499, XP002097744 (see whole document).

Ferrigno, V., et al.,"Use of fructose–1, 6–diphosphate in essential headache. Therapeutic outlook and case study." (Oct. 1987) 68 (10) 51 5–8, Gjiornale Di Clinica Medica.

* cited by examiner

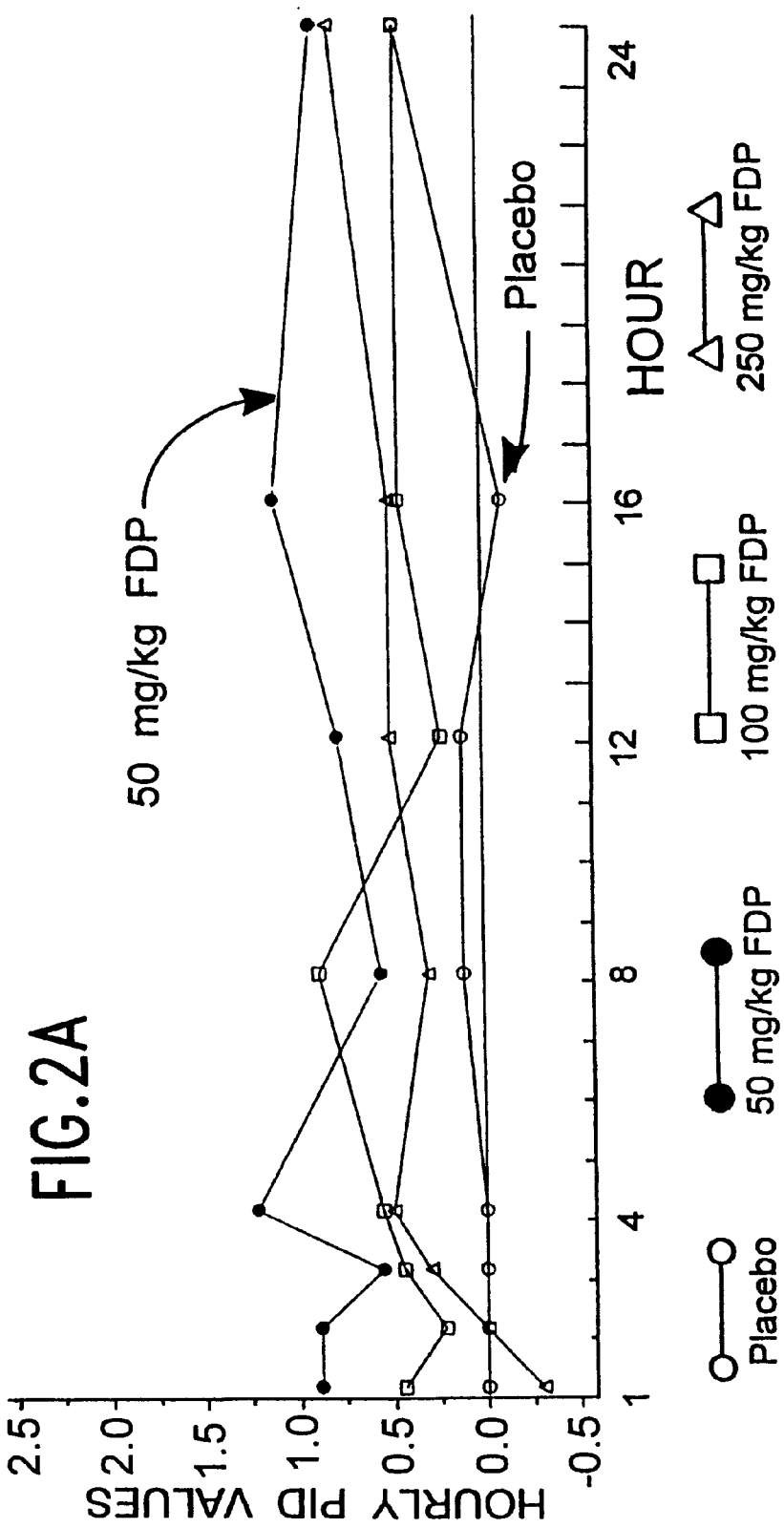

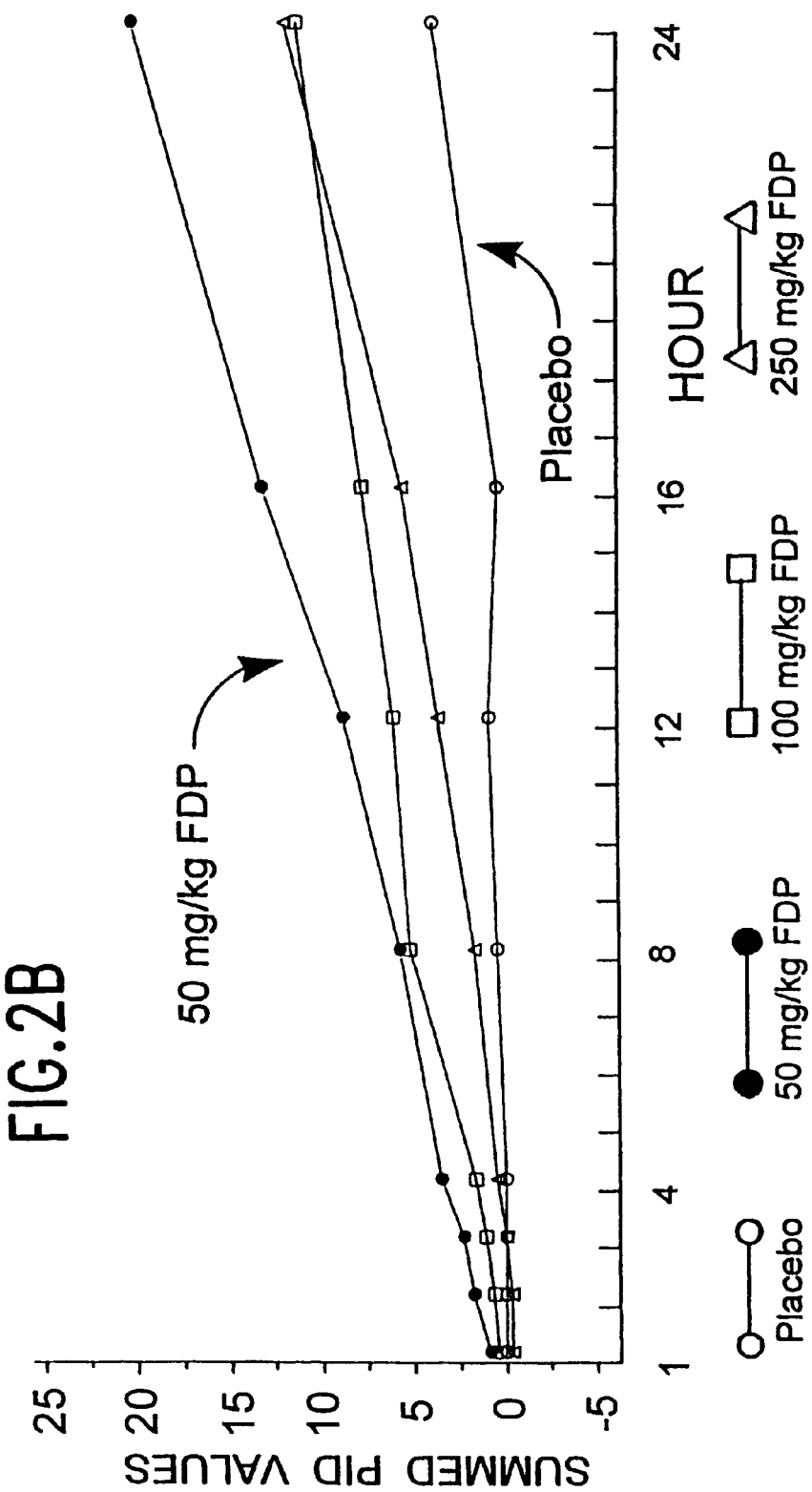

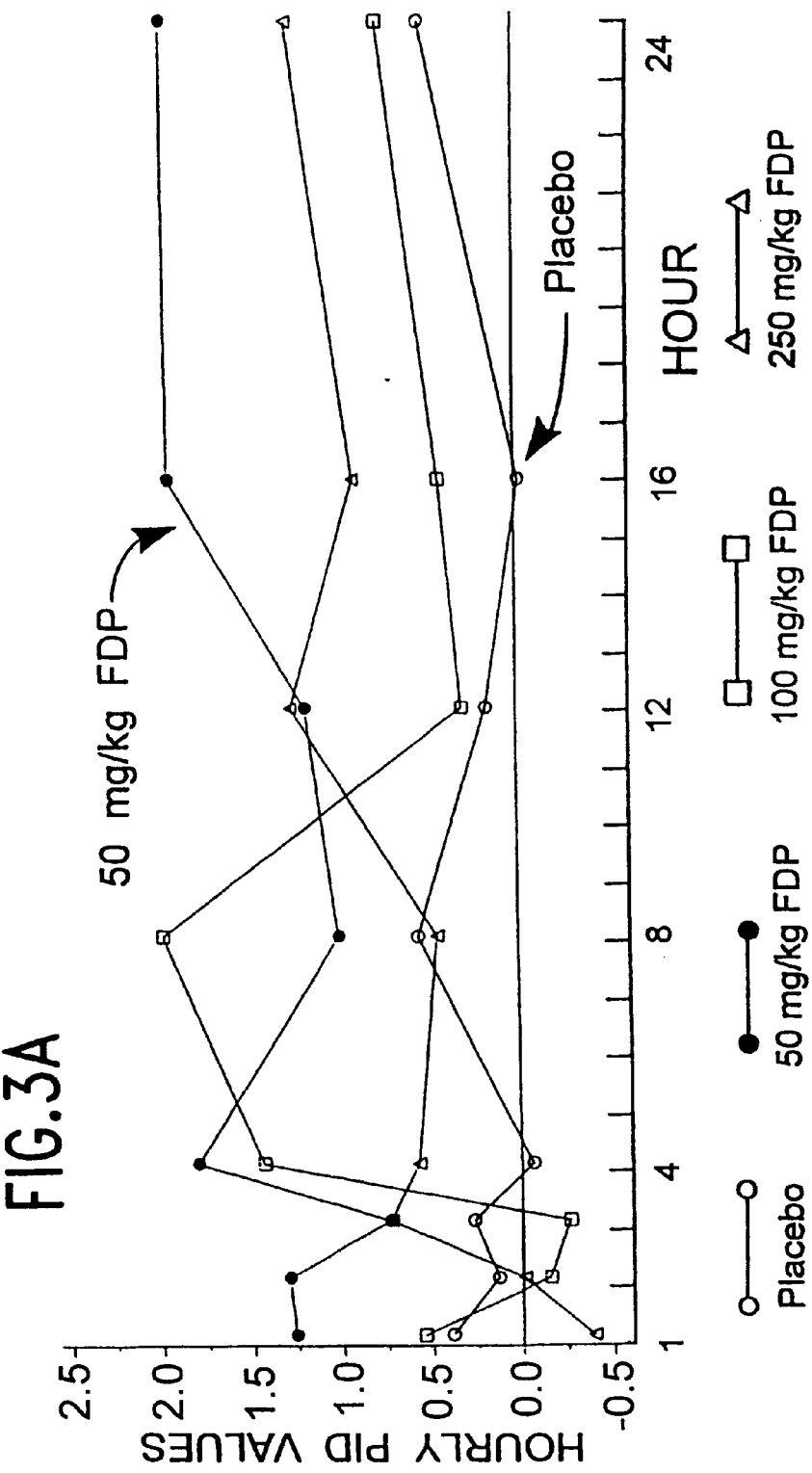

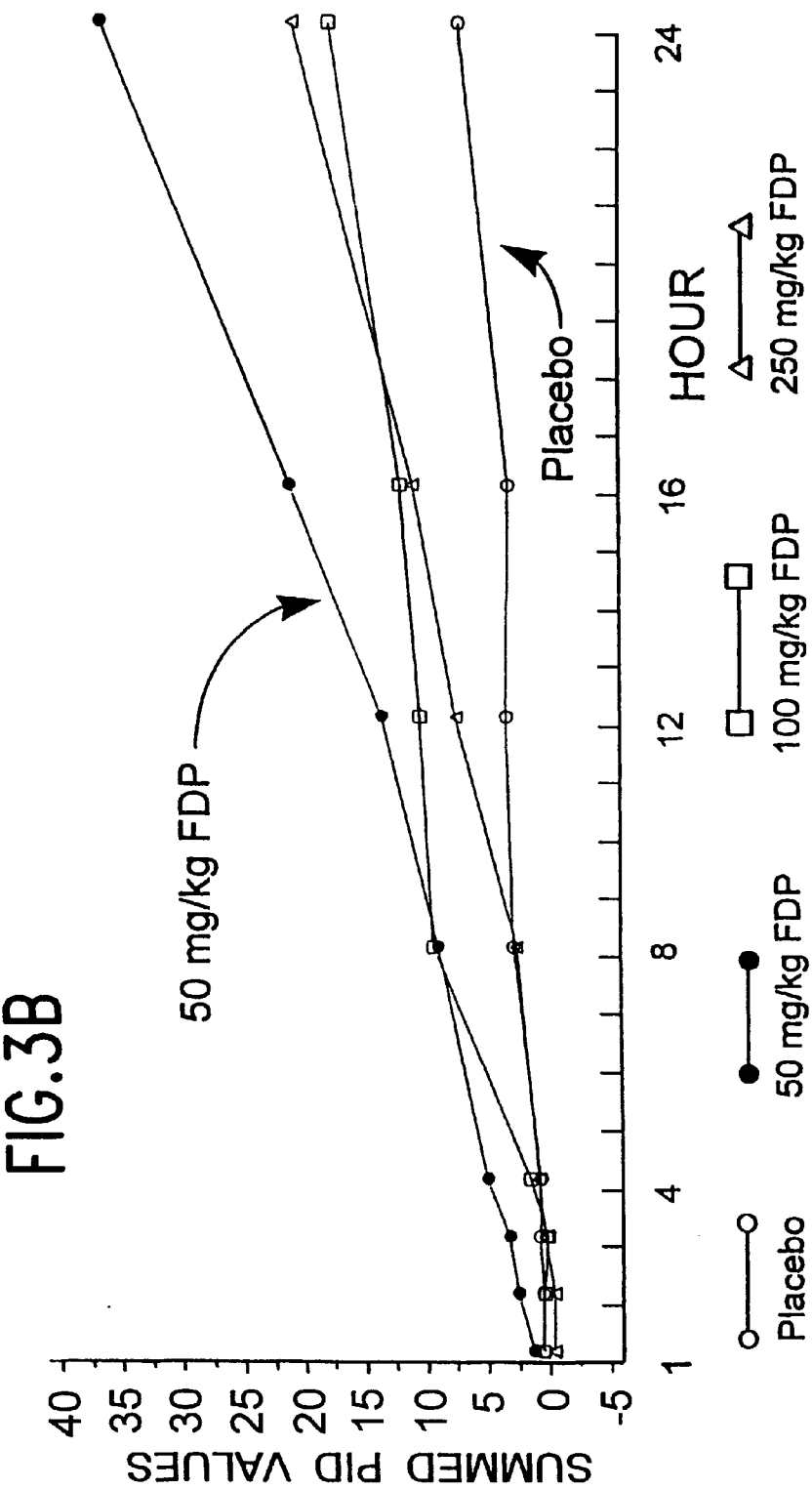

TREATMENT OF SICKLE CELL ANEMIA CRISES WITH FRUCTOSE-1,6-DIPHOSPHATE AS AN ANALGESIC DRUG

This is a continuation of application Ser. No. 08/943,688, filed Oct. 3, 1997 now U.S. Pat. No. 6,074,658.

BACKGROUND OF THE INVENTION

This invention relates to the use of a naturally occurring sugar-phosphate compound called fructose-1,6-diphosphate, for treating the sporadic crises that arise in people suffering from sickle cell anemia.

The following paragraphs provide background information on sickle cell anemia, under its subheading, and then on fructose-1,6-diphosphate, under a different subheading. However, it must be emphasized that fructose-1,6-diphosphate (abbreviated herein as FDP) apparently has never before been used to treat sickle cell anemia. A search of the National -2O Library of Medicine computerized database, combining "sickle cell anemia" or "sickle hemoglobin" with either "fructose diphosphate" or "fructose phosphates" identified only a single article, which involved a different compound. That article, Colomer et al 1991 (complete citations are provided below) related to the levels of fructose-2,6-bisphosphate in certain types of cells, congenital hemolytic anemias. As described below, 2,6-FDP (which is of no interest whatever in the current invention) has very different biochemical properties than 1,6-FDP, which is the compound used in this invention. The 1,6-FDP isomer (with phosphate groups coupled to the #1 and #6 carbon atoms of the fructose molecule) is the only form of FDP that is of interest herein. It is discussed in more detail below.

Accordingly, sickle cell anemia and 1,6-FDP have both been studied extensively. However, there apparently has never been any prior effort to treat sickle cell anemia, using 1,6FDP.

Background Information on Sickle Cell Anemia Sickle cell anemia is a well-known disease, in which red blood cells (abbreviated as RBC's; also called erythrocytes) contain hemoglobin molecules which have a dangerous tendency to crystallize and become non-functional, due to a genetic mutation. In the most common form of this disease, the beta (or B) chain of the hemoglobin protein has a valine residue, instead of a glutamate residue, at the number 6 position. Other substitutions have also been identified, such as "sickle C" disease (which has a lysine residue at the #6 position) and "sickle D" disease (which has a glutamine residue at the #6 residue).

This genetic mutation is relatively common in Africa, since a person who carries a single copy of the mutated gene has a relatively high resistance to malaria, without suffering from major adverse health effects. Accordingly, it has been estimated that roughly 30% of all people native to Nigeria (as just one example) carry at least one such gene (Barnhart et al 1976). About 8% of African-Americans also carry at least one such gene, although local populations often contain higher levels. The gene which disposes red blood cells to sickling is often referred to as HbS, where "Hb" refers to hemoglobin, and "S" refers to sickling. By contrast, a normal, healthy, adult hemoglobin is usually referred to as HbA.

As briefly noted above, a single copy of the gene does not inflict major adverse health effects on the person carrying that gene. Such people are often referred to as "heterozygotes," since they carry two different types of genes (i.e., one is the defective HbS gene, and the other is the normal HbA gene). Usually, only about 40% or less of their hemoglobin is of the sickling variety, while the rest (the majority) is normal. Their red cells will sickle, but only if exposed to hypoxia at much more severe levels than will provoke sickling in homozygotes. Heterozygotes (single-gene carriers) usually have few if any clinical problems, and they do not suffer from reduced life expectancies or increased hospitalization rates.

By contrast, "homozygotes" carry two copies of the defective HbS gene, and do not have any normal and healthy HbA hemoglobin (they may sometimes retain variable amounts of a fetal type of hemoglobin, called HbF, which does not occur in healthy adults). Accordingly, they are the ones who suffer from the debilitating, often devastating effects of sickle cell anemia. They usually suffer severe spleen damage by the age of about 6, and for the rest of their lives, they suffer from elevated levels of gradually accumulating damage to their other organs and tissues, including the liver and kidneys. In the United States, despite having advanced medical care, typical life expectancy for men having the disease is 42 years, and 48 years for women (Platt et al 1994).

The abnormal amino acid residue on the beta chain allows hemoglobin to polymerize, when it is subjected to a condition of even relatively mild hypoxia. This polymerization activity can be observed in intact red cells, or in cell-free hemoglobin solutions. Polymers are typically 14 stranded helices, and are up to 20 nm long. The formation of polymerized hemoglobin inside red cells provokes a change in the shapes and structures of red blood cells, causing an increase in rigidity of the cell wall, and deformation of the cell into a dehydrated, flattened curved shape, which is the classic "sickle" shape (named after the old grain-harvesting tool) that gives the disease its name. Hemoglobin polymerization can also lead to other severely deformed cell shapes, in addition to the sickled shape. For a review of this molecular process and its effects on red blood cells, see Dean and Schechter 1978.

In a patient, these changes in red blood cell shapes may be widespread (for example, during surgery that requires anesthesia), or regional (for example, behind a venous tourniquet when drawing a blood sample). They can also be triggered by events such as bacterial or viral infections, which stress the body (or certain parts of the body) in various ways that can generate localized ischemia and/or hypoxia.

For most patients, sickle cell anemia does not cause constant or chronic pain. However, most sickle cell anemia patients suffer from sporadic yet recurrent episodes that are referred to herein as "ischemic crises" (all references herein to a crisis or crises refer to these sporadic, recurrent crises which occur in the normal course of sickle cell disease; such references do not relate to any other type of ischemic crisis, such as a stroke or heart attack). During such crises, a sickle cell (SC) patient will usually experience severe pain, at one or more locations which frequently vary between patients, and between different crises in a specific patient. It is not uncommon for one or more joints to become swollen and sore, and/or for the patient to suffer from either sharp or diffuse pain in the abdomen, which is presumed to be due to ischemic conditions in one or more portions of one or more organs.

Such crises are generally referred to as ischemic crises, since they typically involve blockade of capillaries and prevention of blood flow into a tissue that becomes starved of oxygen and glucose. This blockade of the capillaries is caused by red blood cells that have lost their normal shape and flexibility, and have collapsed or distorted into the rigid or semi-rigid "sickled" shapes that gives the disease its name. This blockade of capillaries shuts off the flow of fresh blood through those portions of the organ or tissue that are normally serviced by the blocked capillaries. This state of events, due to the sickling of the red blood cells due to the polymerization of HbS-type hemoglobin molecules, leads directly to ischemia, which is the medical term for inadequate blood flow to an organ or tissue.

Most sickle cell patients usually suffer several such ischemic crises per year. During these crises, the patient usually must be hospitalized, restricted to bed rest with little or no exertion, and treated with a variety of drugs, including strong painkillers such as morphine, codeine, and meperidine (also known as Demerol™), and by broad-spectrum antibiotics, both to help control any infections that may be contributing to the crises, and to help prevent or reduce additional infections in tissues or organs that are weakened by the ischemic crisis.

The physiological damage and increased morbidity and mortality caused by sickle cell anemia has been studied extensively (e.g., Platt et al 1994). Briefly, among young children, dactylitis is common, due to ischemic necrosis of the small bones and cartilages of the hands and feet, and acute abdominal pain is often caused by accumulating damage to the spleen. Acute abdominal pain can also be due to liver or kidney infarction, or associated with hematuria. Cholecystitis due to gall stones, aseptic necrosis of the head of the femur, radiologic evidence of widened marrow space in the skull, spinal osteoporosis and renal papillary necrosis typically occur over the age of 10 years, and pathological fractures often supervene in patients greater than 18 years, especially at the head of the femur and the humerus. Leg ulcers are common in adult patients, and lobar pneumonias, pulmonary infarctions, stroke, and retinal lesions may occur. In all cases, the pain is severe, often migratory, and diffuse.

When an ischemic crisis commences, it sets into motion a cascade of events that render the crisis even more severe and difficult to arrest and treat. Three aspects of the cascading, self-perpetuating nature of these ischemic crises are worth noting.

First, as soon as a single problematic cell takes on a semi-rigid shape and gets wedged into a capillary without being able to pass through it, it can trap a substantial number of cells behind it, in the vasculature which leads toward up to the blocked capillary. The trapped cells eventually become depleted of the oxygen, and they too will begin to sickle and die, which aggravates the size and severity of the problem.

Second, the creation of blockage problems in certain parts of a complex fluid-flow network will quickly transfer additional stresses to the other parts of the network. If a segment of tissue that is normally served by two or more capillaries suddenly loses its supply of fresh nutrients and oxygen from one of its suppliers, it will immediately begin placing higher and greater demands on its other suppliers, thereby placing them in danger of becoming overloaded as well, in a way which can threaten to provoke hypoxic sickling of blood cells in other previously unaffected capillaries, which may then shut down those other capillaries as well.

And third, metabolic rates inside red blood cells increase, when the cells encounter the types of stress that provoke sickling. This increase in metabolism is associated with defective ion transport across the red cell membrane, calcium influx, and increased membrane rigidity. In a sense, when a cell encounters the type of stress that can provoke sickling, its internal mechanisms begin trying to work harder, in order to overcome the problem. However, the increased rate of metabolism can quickly deplete the cell's ATP and other resources, thereby leaving the depleted cell even more vulnerable, and at greater risk of collapsing into a full-blown sickled condition.

The only prior treatment for sickle cell anemia that has shown any substantial benefit involves a compound called hydroxyurea. In some patients, this compound can reduce the frequency of sickle cell crises, presumably due to an ability to increase the expression levels of fetal hemoglobin genes. However, this treatment has only limited utility; many patients on hydroxyurea still experience recurrent ischemic attacks, and it is not effective in treating those attacks. Many of the patients in the clinical trial described in Example 6 were already receiving hydroxyurea therapy, when they suffered the crisis that caused them to enter the study described below, involving FDP.

This is a very brief overview of an extraordinarily difficult, burdensome, and expensive medical problem, which faces many millions of people around the globe, and which imposes huge and intractable financial burdens on sickle cell patients, their families, their employers, their health insurers, and their governmental health, housing, and welfare systems. Under current medical practice, there is a major and severe need for better ways to treat sickle cell anemia, both to prevent the recurrent ischemic crises that characterize the disease, and to help treat the extremely painful ischemic crises that play havoc with the lives (and internal organs) of most sickle cell patients, several times a year. The only care such patients receive today, during such crises, is essentially palliative care, which includes days and days of enforced bed rest, broad-spectrum antibiotics, and pain-killing drugs that need to be potent and effective, but which pose a major risk of long-term addiction. Despite all the advances of modern medical practice, sickle cell anemia remains a severe and debilitating disease, with no effective cure or treatment.

As noted above, there has not been any previously reported effort (to the best of the Applicant's knowledge), by anyone, to use fructose-1,6-diphosphate (FDP) to treat sickle cell anemia, or even to test FDP to determine whether it might be effective in treating sickle cell patients. That point needs to be kept in mind during the next section, which describes the prior art relating to FDP.

Background Information on 1,6-FDP

Fructose-1,6-diphosphate (FDP) is a naturally occurring sugar-phosphate molecule, which is created and then quickly consumed as an intermediate during the series of reactions that make up glycolysis (i.e., the series of reactions by which glucose is metabolized, to release its stored energy). As a short-lived intermediate that is quickly consumed, FDP normally is present in cells only at relatively low concentrations.

It should be noted that some scientists refer to FDP as fructose-1,6-biphosphate, or fructose-1,6-bisphosphate. The 1,6-isomer of fructose diphosphate, which contains phosphate groups bonded to the #1 and #6 carbon atoms of the fructose molecule, is the only isomer of interest herein. Other isomers (such as fructose-2,6-diphosphate) are not relevant herein, and are excluded from any references herein to FDP or fructose diphosphate.

From an energy-containing standpoint, FDP is at the highest point in the pathway of glycolysis; two molecules of energy-rich ATP have to be used, in order to convert the initial glucose molecules into FDP. Starting with FDP, all remaining reactions in the pathway of glycolysis release, rather than consume, energy.

Because of FDP's vantage point at the highest energy plateau of the energy-generating process of glycolysis, which is absolutely essential to all cells, numerous medical and scientific articles have suggested that FDP might potentially be useful as a medical treatment for patients and victims suffering from medical crises such as strokes or brain injury, cardiac arrest, heart attack, suffocation, loss of blood due to injury, shooting, or stabbing, etc. Examples of such articles include Markov et al 1980, 1986, and 1987, Cacioli et al 1988, Lazzarino et al 1989, Crescimanno et al 1990, Myers et al 1990, Gregory et al 1990, Nakai et al 1991, Gobbel et al 1994, Hardin et al 1994, Kelleher et al 1995, and Sano et al 1995. Relevant U.S. patents include U.S. Pat. Nos. 4,546,095 (Markov 1985), 4,703,040 (Markov 1987), and 4,757,052 (Markov 1988).

Despite all of these published articles and patents, which stretch back nearly 20 years, to at least 1980, a high degree of skepticism and reluctance still exists regarding the use of FDP for any medical purpose. Except for a few small and very limited clinical trials, FDP simply is not used or prescribed by any practicing physicians, for any reason or for any medical purpose, except possibly in a few foreign countries such as China and Italy.

The absence of any actual use of FDP on patients (many of whom desperately need the energy supplies that might be derived from FDP, as they are dying of massive heart attacks, cardiac arrest, strokes, or blood loss) is believed to be due to a number of factors, including the following:

(1) FDP is a diphosphate with a strong negative charge, and doctors and researchers widely assume that its strong negative charge will prevent it from entering cells in any significant or useful quantity. Since energy metabolism and glycolysis occur inside cells, it is assumed that FDP will not get to the sites where it is needed, in sufficient quantities to do any significant good.

(2) It is also believed that FDP has a very short half-life in the blood, and will effectively disappear from the blood within a few minutes after injection or infusion. (3) In nearly all types of cells (other than red blood cells, which do not have mitochondria, and which do not engage in aerobic glycolysis), the amount of energy generated during glycolysis (i.e., the conversion of glucose to pyruvic acid) is only a small fraction of the energy generated by the aerobic (Krebs Cycle) oxidation of pyruvic acid, to form carbon dioxide and water. Therefore, under conditions of tissue ischemia or hypoxia, where an oxygen deficit blocks aerobic conversion and causes the creation of lactic acid instead, it is generally assumed that FDP infusion would be insufficient to supplement ATP levels to a degree that can significantly aid cell survival.

(4) Under conditions of ischemia or hypoxia, an injection of FDP into a patient would lead directly to substantial increases in lactic acid levels; for example, when radiolabelled FDP was added to intact isolated hearts that were being perfused, nearly 90% of the exogenous FDP was converted into lactic acid, and only about 10% of the FDP was fully oxidized to carbon dioxide (Lazzarino et al 1992). This effect from an FDP injection could be very harmful, since excess lactic acid can poison an enzyme called phosphofructokinase (PFK), which is a crucial rate-limiting enzyme in glycolysis (e.g., Hoffman 1976; Kubler and Spieckerman 1978; Opie 1968). The potential costs and risks of providing a relatively small quantity of energy (via FDP infusion into ischemic tissue) is very high. If the PFK enzyme is inhibited or poisoned by lactate (which is produced from FDP at a nearly 90% rate, in ischemic tissue), then it is widely assumed that the overall result of FDP administration might well be to inhibit or even shut down the much more useful and productive aerobic (Krebs) pathway which leads to carbon dioxide.

(5) Drug intervention in acute ischemic trauma has proven to be extremely difficult and complex, for a large number of reasons. Among other things, it often requires 1 to 3 hours (or more) before a patient can be properly diagnosed in a manner that justifies the use of a specific drug. This is aggravated by the fact that there are, for example, three major categories of shock, and proper treatment for one type can actually increase the damage suffered by someone who is suffering from a different type of shock. To avoid any liability for improper care, ambulance attendants and other emergency-care providers simply cannot and do not take the risk, in most cases, of trying to treat someone suffering from shock or other medical crises of unknown origin. However, by the time someone arrives at a hospital emergency room and is adequately diagnosed so that focused drug treatment can begin, too much time has often elapsed, and any drugs administered there are often too late to prevent any cell death and permanent tissue damage that has already occurred.

(6) Contrary to the articles cited above which report that FDP may have beneficial effects in certain types of lab tests, a number of other articles have reported that FDP had no beneficial effects in other studies. Examples of these negative articles include Eddy et al 1981, Pasque et al 1984, Tortosa et al 1993, and Angelos et al 1993.

For these and other reasons, it appears that little if any effort has been directed by the pharmaceutical industry toward developing FDP as a useful drug. Under the laws enforced by the U.S. Food and Drug Administration, FDP cannot be sold in the United States for administration to human patients by physicians. With the possible exception of a few small clinical trials, FDP simply is not administered to any patients, anywhere in the United States, regardless of how desperate their plight may be following a stroke, cardiac arrest, shooting, stabbing, or other medical crisis.

More importantly for the subject invention, FDP apparently has never previously been used (or even tested) for treating patients suffering from sickle cell anemia, either for long-term care, or for treating the recurrent ischemic crises caused by sickle cell anemia.

Additional Difficulties in Evaluating Candidate Treatments

There are several additional factors that have severely thwarted further progress in efforts to treat sickle cell anemia. These factors need to be understood and evaluated carefully, in evaluating any such efforts to find ways to overcome these extraordinary difficulties.

First, it should be noted that there are no accepted animal models for studying sickle cell anemia. This makes research on potential treatments for sickle cell anemia substantially more difficult, expensive, and risky. Preliminary tests can be done on an in vitro basis, using red blood cells in blood samples or in cell incubation media. However, if those test results seem satisfactory, there is no middle plateau that allows testing on mice, rats, dogs, or any other type of lab animal. Instead, a giant leap must be made from in vitro tests, all the way up to human clinical trials, which are extremely expensive, liability-laden, and risky. This factor has severely aggravated the lack of more progress toward finding effective treatments.

In addition, the tendency of sickle cell anemia to cause very different types of physiological damage, in different patients, poses even more difficulty in proving that any particular treatment is indeed useful and effective. Damage caused by sickle cell disease can be manifested in nearly any of the internal organs, and the actual pattern of damage that appears in any specific patient is nearly impossible to predict. Furthermore, each type of damage that appears in the various organs is similar to the damage caused by various other diseases and etiologies. In addition, as noted above, the damage tends to accumulate slowly, over a period of decades.

All of these factors, acting together in human patients, make it extraordinarily difficult to develop any treatments that might be able to help ameliorate the symptoms or damage of sickle cell disease, because it is painfully clear, to any pharmaceutical company that might be considering investing in any such research, that it will never be able to obtain approval, from the U.S. Food and Drug Administration or from any of the comparable agencies in other countries, to sell its new drug as an approved therapy for treating sickle cell anemia, unless it can submit trial data which clearly prove that the treatment actually works, in humans. The difficulties that must be overcome to actually prove that a drug can reduce the damage of a disease which takes decades to fully inflict and manifest its damage, and affects different specific patients in very different ways, are extraordinary. These obstacles have severely retarded any progress (or even research) toward effective treatments for sickle cell anemia, and these factors cannot be ignored when evaluating a new treatment, as set forth in the current invention.

However, these confounding factors have been avoided, by the decision of the Applicant company to focus on an entirely different category of treatment outcome, which has never previously been considered significant in any other research to evaluate the effects of FDP. This treatment outcome involves the measurement of pain, which requires patients to answer questions ("How much does it hurt?") that require subjective opinions, rather than objective data that can be measured by mechanical devices or chemical reactions.

This newly adopted goal of the planned research raised its own set of questions, doubts, and risks, and it should be noted that this research project was proposed, in detail, in a grant application that was submitted to the National Institutes of Health. That grant application was rejected, by the experts who reviewed that proposal. However, the researchers who were planning the clinical trials described herein deemed this approach to be necessary, as the only practical way to gather useful data that could overcome the difficulties that have confounded other efforts to prove (to the satisfaction of the Food and Drug Administration) the efficacy of candidate treatments for sickle cell disease.

Accordingly, the primary question that was addressed in these clinical trials was the reduction of pain, i.e., the efficacy of FDP as an analgesic drug. This was a highly unusual and non-obvious approach, given the fact that FDP has never previously been reported to offer analgesic (pain-controlling) activity, in any other treatment setting. To the best of the Applicant's knowledge and belief, this is the first-ever disclosure that FDP has analgesic activity, in any situation.

Therefore, one object of the subject invention is to provide a method for reducing pain in patients who suffer from sickle cell anemia, during the recurrent ischemic crises that are attributable to the disease, by disclosing (for the first time) that fructose-1,6-diphosphate (FDP) actually has effective analgesic activity, in such patients, during such crises.

Another object of this invention is to disclose that FDP can reduce the length of hospital stays that are necessary to cope with recurrent sickling crises in sickle cell patients, and can also reduce the need for potentially addictive painkillers such as morphine and other opiates.

Another object of this invention is to provide a medical treatment for recurrent sickle cell anemia crises, for use in conjunction with other medical treatments that are conventionally used during such crises, in a manner which does not interfere with such other treatments and which reduces pain for the patient and helps facilitate and speed up satisfactory resolution of the crisis, thereby allowing the patient to spend less time in a hospital or other such medical facility.

Another object of this invention is to disclose a method of reducing the accumulative permanent damage that is inflicted on sickle cell patients, by reducing both (1) the amount of damage that organs and tissues suffer due to ischemia caused by blockage of blood flow through capillaries, and (2) the amount of damage caused by oxidative free radicals, in organs and tissues where blood flow has been restored after a period of ischemia.

These and other objects of the invention will become more apparent through the following summary, drawings, and description of the preferred embodiments.

SUMMARY OF THE INVENTION

This invention discloses that fructose-1,6-diphosphate (abbreviated as FDP) has been shown, in double-blinded placebo-controlled clinical trials on patients suffering from sickle cell anemia, to substantially reduce the pain that is suffered by such patients during recurrent ischemic crises that involve cell sickling. Controlled clinical trials on human volunteers who have been hospitalized for treatment of such crises demonstrated that when such patients receive an intravenous injection of 50 mg/kg FDP, they reported substantially lower pain levels during their hospital stays than placebo-controlled test groups that did not receive FDP, but who received otherwise identical treatment.

Apparently, FDP has never previously been used, or even tested in any human trials, to treat sickle cell anemia; in addition, FDP has never previously been reported to have any analgesic (pain-reducing) activity.

In addition to providing a direct benefit in its own right, the demonstrated reduction in pain during cell sickling crises indicates that FDP also has other beneficial long-term effects, in preventing and reducing permanent damage that is being inflicted on organs and tissues by ischemic starvation, caused by sickled blood cells which clog and block the capillaries that serve the organs and tissue.

The beneficial effects of FDP in treating blood cells from patients who suffer from sickle cell disease also have been demonstrated in a range of in vitro tests. These cell incubation tests include demonstrations that (1) FDP can increase adenosine tri-phosphate (ATP) levels inside red blood cells from sickle cell patients; (2) FDP can reduce the extent to which such cells deform into sickled shapes when subjected to hypoxic stress; (3) after red blood cells from sickle cell patients have deformed into sickled shapes, due to stress, FDP can help such cells return to their proper non-sickled shapes when the cells are reoxygenated; (4) FDP can reduce the extent to which red blood cells hemolyze (rupture) when they are subjected to stress; and (5) FDP can help red blood cells from sickle cell patients remain flexible and deformable, which is an essential trait of healthy red blood cells, despite being subjected to hypoxic stress.

All of these results, from both in vitro (cell incubation) tests and from human clinical trials, clearly show that FDP can offer substantial benefits to sickle cell patients. The various mechanisms of action of FDP also suggest that it can be co-administered along with any other drugs that are useful for treating sickle cell crises.

It is also disclosed herein that the Applicant company, Cypros Pharmaceutical corporation, has created a new and proprietary method for creating FDP in sterile form which has a shelf life of months and possibly even years, as a semi-lyophilized powder or cake having a relatively high residual water content of about 10% to about 25% by weight. This method, which is being patented separately, overcomes previous problems of impurities, chemical instability, short shelf life, and non-sterile bulk preparative methods that have hampered previous efforts to study or use FDP for medical purposes.

BRIEF DESCRIPTION OF THE DRAWINGS

FIG. 2 contains two related graphs, showing how intravenous infusion of FDP caused analgesic (pain-reducing) effects in sickle cell patients. Raw data was gathered by having patients in each treatment group evaluate their pain levels on a numerical scale (0=no pain; 5=intense pain), beginning shortly before an intravenous infusion of FDP, and repeatedly over the next 24 hours. The pain scores (mean values) at each testing period were then compared to the baseline (pre-FDP) scores, to determine "pain intensity differential" (PID) values. The top graph, FIG. 2A, displays ongoing PID values (i.e., the amount of improvement or deterioration, compared to the baseline value, for each reporting time). The bottom graph, FIG. 2B, displays "summed PID" (SPID) values (effectively, the area under the curve in FIG. 2A). These data show that FDP significantly helped reduce pain levels.

FIG. 3 contains two graphs showing the same types of data as in FIG. 2, with ongoing PID values on tip and summed PID values on the bottom. To act as a control on the numerical scores, and to help avoid any problems with language or reading skills, these data were gathered by having each patient make a mark on a 10 centimeter horizontal line, which offered a visual scale for ranking pain intensity (left end=no pain; right end=intense pain).

DESCRIPTION OF THE PREFERRED EMBODIMENTS

Figure 1A:
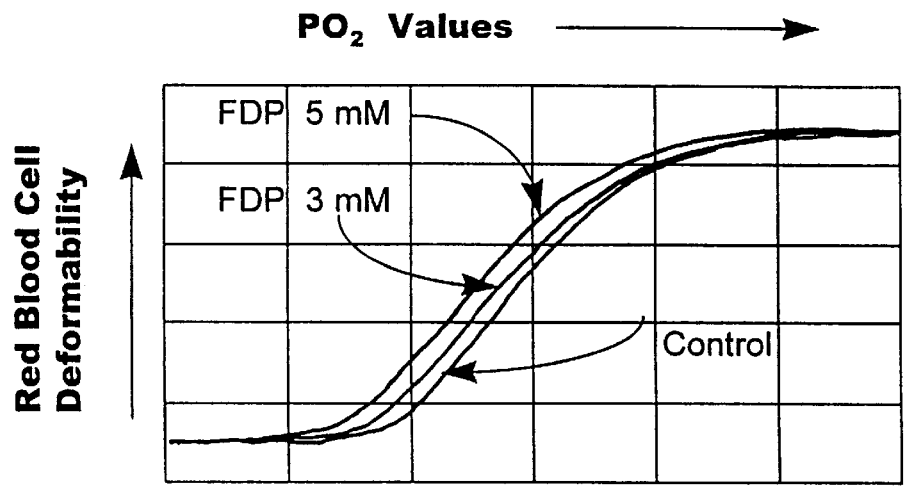
FIG. 1 contains three related graphs, showing that FDP increased the flexibility and deformability of red blood cells from sickle cell patients (see Example 5). Red cells must flex and deform, in order to pass through capillaries. When red cells begin to deform and sickle under hypoxic conditions, they lose their flexibility and assume rigid, dehydrated shapes, causing them to clog and block capillaries, which leads to ischemic crises. Accordingly, the ability of FDP to increase deformability in cells from sickle cell patients, despite hypoxic stress, is highly useful.

This invention discloses that when fructose-1,6-diphosphate (abbreviated as FDP) is administered at a suitable dosage to a patient who is suffering from an ischemic crisis caused by sickle cell anemia, the FDP treatment can substantially reduce the pain being suffered by the patient, and can help reduce the need for morphine and other potentially addictive pain-killing drugs. Controlled clinical trials on human volunteers who have been hospitalized for treatment of such crises demonstrated that when such patients receive FDP, they reported substantially lower pain levels during their hospital stays than control patients who did not receive FDP, but who received otherwise identical medical treatment.

In addition to providing a direct benefit in its own right, a reduction in pain during a sickle cell anemia crisis indicates that FDP has beneficial long-term effects as well, in preventing and reducing the accumulating and permanent types of damage that are being inflicted on organs and tissues by ischemic starvation, as caused by sickled cell clogging and blockade of the capillaries that serve the organs and tissue which are generating the pain that arises during an ischemic crisis.

The beneficial effects of FDP in treating sickle cell disease have been demonstrated, apparently for the first time, by various researchers working for the Applicant company, in a number of different types of tests. In general, these tests can be divided into two categories: (1) in vitro (cell incubation) tests on red blood cells (RBC's) outside of the body, and (2) in vivo tests on human volunteers who suffer from sickle cell anemia, and who arrive at the hospital study site because they need treatment for an active ischemic crisis.

In Vitro Tests on Red Blood Cells

In the first set of in vitro tests on red blood cells, described in detail in Example 1, RBC's were treated with FDP, and then measured for their intracellular levels of adenosine triphosphate (ATP), which is a crucial high-energy compound that can release energy to drive other biochemical reactions inside the cells. In this type of test, high concentrations of ATP inside RBC's indicate that the RBC's are well-supplied, and can carry out their desired metabolic functions. By contrast, lower levels of ATP inside RBC's indicate that the cells have become depleted, and are at substantially higher risk of deforming or collapsing into a semi-rigid sickled shape, which is highly undesirable, since sickled blood cells can block capillaries, triggering an ischemic crisis. A direct correlation between low ATP levels in red blood cells, and the risk and rates of sickling of the cells, has been reported by numerous researchers and is well known.

As described in Example 1, FDP treatment of RBC's was able to substantially increase the level of ATP inside the cells. This was an important demonstration, and this result was not merely predictable and expected, since the general assumption is that FDP cannot readily cross cell membranes, since it has a strong negative charge (due to loss of multiple hydrogen protons from the two phosphoric acid groups). Accordingly, the proof that FDP can indeed increase ATP levels, inside the treated red blood cells of patients who suffer from sickle cell anemia, was an important demonstration, which apparently had not been previously reported.

In a similar but distinct set of tests, described in Example 2, FDP was tested to determine whether it could reduce the sickling activity of red blood cells from sickle cell patients. These tests used hypoxia (i.e., oxygen deprivation) as a method of inducing sickling activity. The hypoxia was generated in either of two ways: (1) chemically generated by treating the cells with a 2% solution of sodium bisulfite, or (2) culturing the cells beneath a blanket of inert nitrogen gas rather than air with oxygen. The results of both types of tests showed that FDP substantially reduced the tendency of the cells to sickle, while glucose treatment offered no advantage.

In another set of tests, described in Example 3, FDP was shown to be capable of helping reverse RBC sickling activity that had already commenced. These tests were carried out by rescuing cells that were subjected to hypoxia (as described in Example 2), dividing them into treatment groups, treating some groups with FDP and other groups with glucose, and exposing the various cells groups to oxygen-containing atmospheres again. The results showed that FDP helped promote the recovery of normal cell shape by the hypoxia-treated cells, while glucose failed.

In yet another set of tests, described in Example 4, FDP was shown to reduce cell breakage and potassium release, in cells that had been subjected to stress; the model used in those experiments involved a reduction in temperature, which slows down the metabolism of ATP, which in turn interferes with proper functioning of the cellular sodium pumps.

An additional set of in vitro tests using red blood cells from sickle cell patients is described in Example 5. In these tests, treatment of the cells with FDP caused the blood cells to retain their flexibility and capacity for deformation. This was a very important showing, since flexibility and capacity for deformation is an essential trait in red cells, which must be able to squeeze through capillaries having internal diameters that are only about half the width of resting red blood cells.

In summary, the data from studies on red blood cells from sickle cell patients (with homozygous sickling genes) demonstrate that FDP appears to offer a number of potentially important advantages, including:

1. FDP can increase ATP levels inside the cells;
2. FDP can reduce sickling of red blood cells in response to hypoxia;
3. FDP can help red cells that have previously sickled, due to hypoxia, recover their original and proper shape after they are reoxygenated;
4. FDP can reduce hemolysis and potassium release by stressed red blood cells from sickle cell patients; and,
5. FDP can help red cells from sickle cell patients maintain flexibility and deformability despite being subjected to hypoxia.

In Vivo Tests on Sickle Cell Patients In Crisis In addition to the cell tests described in Examples 1 and 2, the Applicant carried out a full-scale clinical trial, on human patients actively suffering ischemic crises due to sickle cell anemia. These human clinical trials were carried out at four different teaching hospitals, located in areas that serve predominantly African-American communities with large numbers of sickle cell patients.

In these trials, sickle cell patients who were suffering an active and ongoing ischemic crisis which was severe enough to require hospitalization were divided into a test population, and a control population. The control patients were given a placebo, while the test patients had FDP (which is clear and colorless when dissolved in water) added to the fluids that were being injected into the patients. The treatments were double-blinded; no one receiving either a placebo or FDP knew whether FDP had been added to their injection fluids, and even the doctors and nurses who were administering the fluids did not know what was in each number-coded batch of powder that was added to an injection bag or bottle.

Both sets of patients were carefully selected, and kept closely in balance with each other regarding any potentially conflicting variables, using entire lists of inclusion and exclusion criteria that were carefully planned and evaluated before the study was commenced. The inclusion criteria required that any patient had to meet each and all of the following requirements: (1) patients had to be over the age of 12 years; (2) patients had to weigh more than 40 kg (about 90 pounds); (3) patients had to have a documented history of sickle cell crisis, and be known personally to the chief investigator at the hospital site; and (4) patients had to be experiencing a crisis which was diagnosed by a qualified physician as being similar to other crises that had been observed during previous admissions. In addition, all patients had to provide written informed consent in their primary language, using documents and procedures approved by an impartial Institutional Review Board (IRB).

The exclusion criteria were equally important in carrying out the study. Any candidate was excluded if he or she (1) suffered from any form of thalassemia; (2) was adjudged by a qualified physician to have a hemolytic tendency for any other known or unknown cause, other than sickle cell disease; (3) had been exposed to opiates of any sort (legal or illegal, prescribed or non-prescription), or other "street drugs" within 48 h prior to study; (4) was not alert, could not communicate in an acceptable language with the investigator, or was incoherent or otherwise unable to provide informed consent; (5) had a history of fructose intolerance; (6) suffered from a pre-existing hyperphosphatemia for any reason; or (7) suffered from renal failure due to any cause (including the then-current sickle cell crisis) with serum creatinine levels higher than 2.2 mg/dL. Also, any candidate was excluded if it was anticipated that a potential need for surgery within 8 hours after the infusions posed a significant risk.

If all of these criteria were met, a patient could be enrolled in the study and was assigned to either a control group or an FDP-treatment group. As various patients entered the study, all groups were kept balanced for all known potentially relevant factors, such as age, gender, and weight.

After admission to the hospital, all test subjects were stabilized for at least four hours, and a baseline (i.e., prior to FDP infusion) "pain intensity" score was reported by each patient, using two different reporting scales on a single sheet of paper. One scale used numbers, where 0=no pain, 1=mild pain, 2=moderate pain, 3=severe pain, 4=very severe pain, and 5=worst possible pain. To help confirm the numerical reports, and to provide more assistance to patients who did not have good reading skills, the other scale required the patient to make a mark somewhere on a horizontal line that was 10 centimeters long, with a happy face at the left end beneath the phrase "No pain", and an unhappy face at the right end beneath the phrase, "Pain as bad as it possibly could be". The length of the line (10 cm) allowed an exact numerical value to be easily assigned to each mark, by measuring how many centimeters the mark was positioned from the left end of the line.

After the baseline pain intensity value was marked, FDP was infused into the patient. Three different dosages (50, 100, or 250 mg of FDP per kilogram of patient body weight) were tested, along with a placebo control. To preserve blinding, all three dosages and the placebo were mixed in a constant volume of clear liquid, for infusion.

At 1, 2, 3, 4, 8, 12, 16, and 24 hours after the FDP infusion began, the patients again reported the severity of the pain they were feeling, using the same numerical and visual scales. Mean values were determined for each treatment group, at each time (including the baseline reports).

The post-treatment values for each treatment group were compared against the pre-treatment (baseline) values, to determine "pain intensity differential" (PID) values. These values are indicated in FIGS. 2 and 3. In each figure, the top graph indicates the ongoing or current PID value, at that particular reporting time. The paired bottom graph indicates the summed PID values for all times up to and including that reporting period; in essence, the SPID values in the bottom graphs indicate the areas under the curves in the top graphs, which effectively indicates how much total (i.e., time-dependent) relief from pain was provided by the FDP treatment.

As indicated in both figures, the FDP treatment provided substantial relief, compared to the placebo. As discussed below, the 50 mg/kg dosage provided the best relief in the particular test conditions used in these tests, which involved a single injection of FDP over a 30 minute period. As discussed below, it is believed that better results would likely be available from higher dosages, if a series of intravenous infusions were spread out over longer periods of time.

Creation of Sterile, Stable, Semi-Lyophilized FDP

It is also disclosed herein that the Applicant company has created a new and proprietary method for creating FDP in sterile form which has a shelf life of months or even years without requiring refrigeration, as a semi-lyophilized powder or cake having a relatively high residual water content. The residual water content is about 10% to about 25% by weight; by contrast, most lyophilized drugs that have been prepared for injection into humans have a residual water content of only about 1 to 2%.

This method is described in detail in U.S. patent application Ser. No. 08/705,773, which is also assigned to the same Applicant company (Cypros Pharmaceutical Corporation, of Carlsbad, Calif.) which owns this current application on treating sickle cell anemia, and which designed and funded the clinical trials described herein. The teachings of U.S. application Ser. No. 08/705,773 are incorporated herein by reference. That application has received a Notice of Allowance, and is expected to issue as a U.S. patent in early 1998.

These sterile, stable FDP preparations overcome the problems that have severely hampered prior efforts to study or use FDP for medical purposes. Prior to the development of this form of partially lyophilized FDP (which is not yet commercially available) by Cypros Pharmaceutical Company, there have been only two known preparations of FDP which are commercially available anywhere in the world, other than research reagents that are sold in gram or milligram quantities by specialty chemical companies. One of these preparations is a non-sterile bulk powder, manufactured in Germany by Boehringer Mannheim. This bulk material cannot be used for injection into humans, since it does not meet the sterility requirements that apply to injectable drugs.

The other commercially available FDP formulation is a lyophilized preparation that is manufactured in Italy by a company called Biochemica Foscama. To the best of the Applicant's knowledge and belief, it is manufactured by steps that include pouring a large batch of an aqueous mixture of FDP into a large tray, freezing the mixture and subjecting it to a vacuum to remove the water, thereby creating a large solidified cake, grinding or milling the large cake into small particles, loading the ground-up particles into small vials, and sealing the vials. This process is not well-suited for creating a sterile and stable drug for injection into humans. To the best of the Applicant's knowledge and belief, Biochemica Foscama has never made any effort to obtain permission from the U.S. Food and Drug Administration to sell their FDP preparations in the United States, for use on humans.

Accordingly, the new methods developed by the Applicant herein, Cypros Pharmaceutical Company, overcome the previous problems of sterility, purity, and chemical instability that have prevented any previous FDP preparations from receiving the governmental approvals that are necessary to qualify a drug for widespread use in humans. The manufacturing methods developed by the Applicant company are well-suited to create completely sterile, stable, pure injectable drugs that can and will gain full approval by the appropriate government agencies in the U.S. and elsewhere, for use in humans.

Dosages and Modes of Administration

The preferred mode of administration of FDP, for treating sickle cell anemia crises, is intravenous administration of FDP dissolved at a suitable concentration (such as about 5 to about 20%, weight per volume) in a suitable aqueous carrier liquid, such as a normal saline solution. Sugar-containing carrier liquids (such as Ringer's lactate, or other glucose or dextrose solutions) can also be used if desired, provided that the total sugar content does not cause undesired levels of lactic acidosis. Intravenous administration can be either through bolus injection (preferably several times per day), or through continuous infusion over a sustained period of time. Total preferred dosages for bolus injection or infusion may vary substantially, depending on a patient's physical condition; in general, they will usually range from about 25 mg/kg to about 250 mg/kg. Total preferred daily dosages will also vary substantially between different patients; in general, a range of about 40 to about 1000 mg/kg, during the first day of a hospital stay, are anticipated, while preferred dosages on the second and subsequent days will depend on various changes in the patient's medical condition during the course of the hospital stay.

It should be noted that the tests described in Example 6 (the results are displayed in FIGS. 2 and 3) studied three different dosages (50, 100, or 250 mg of FDP, per kilogram of patient body weight), in a single-dose infusion over a 30 minute period. In those particular tests, the smallest dosage tested (50 mg/kg) had the best efficacy. This is presumed to be due to slightly increased levels of lactic acidosis, at the higher single-bolus dosage levels. It is believed and anticipated that better results would likely be available from higher dosages, if intravenously infused dosages of FDP are spread out over longer periods of time.

EXAMPLES

In all examples, any reference to "patient" or "volunteer" refers to a patient who suffers from sickle cell disease, and who has homozygous HbS genes for the disease (i.e., a sickling hemoglobin gene was inherited from each parent, so that the person has two sickling hemoglobin genes, and no properly functioning hemoglobin genes). Unless otherwise noted, any reference in the examples to "cells" refers to red blood cells (erythrocytes) from such patients.

Example 1

Ability of FDP to Increase ATP Levels Inside Red Blood Cells

Whole blood samples were taken from patients who suffer from sickle cell disease, but who were not suffering an ischemic crisis at the time; their hematocrit values averaged 24% ±6%. Paired samples (4 mL) from each patient were treated with either FDP (5% aqueous solution, 2.5 mg/mL), or with an equivalent amount of glucose. The paired samples were incubated at 37° C. for 25 minutes, and were then homogenized, and deproteinized with 6% perchloric acid. The samples were centrifuged at 4° C., and the supernatant was assayed for ATP, di-hydroxy acetone phosphate (DHAP), pyruvate, and lactic acid.

As a control, whole blood samples were also taken from normal volunteers without any sickling HbS genes (hematocrit =41±4%); such samples were taken both before, and 30 minutes after, an intravenous infusion of FDP in aqueous solution, at dosages of 75 mg/kg (i.e., 75 milligrams of FDP per kilogram of patient body weight). The cells were processed as described above, and the supernatants were tested for ATP levels.

The results are provided in Table 1. In this table, ATP and DHAP values are in micromoles per milliliter; pyruvate values are in milligrams per 100 milliliters; and lactate values are in milligram percent.

TABLE 1

EFFECT OF FDP ON ATP LEVELS INSIDE RED CELLS

|  | ATP | DHAP | Pyruvate | Lactate |
|---|---|---|---|---|
| Sickle cells, glucose-treated | 1.04 ± 0.01 | 0.14 ± 0.03 | 0.59 ± 0.09 | 46.6 ± 2.59 |
| Sickle cells FDP-treated | 2.17 ± 0.13 | 1.23 ± 0.05 | 1.52 ± 0.01 | 36.2 ± 2.16 |
| Normal cells, before FDP infusion | 2.88 ± 0.13 | 0.05 ± 0.04 | 1.20 ± 0.07 | 7.66 ± 0.16 |
| Normal cells, after i.v. FDP infusion | 3.29 ± 0.16 | 0.08 ± 0.05 | 1.08 ± 0.08 | 6.34 ± 0.55 |

These results indicate that treatment with FDP more than doubled the ATP concentrations, in red blood cells from patients with sickle cell anemia. FDP also increased the levels of pyruvate and DHAP (both of which are useful metabolites). In sickle cell patients, each of these effects was statistically significant at a level of 99.5% or higher, and each of these effects of FDP on red blood cells are useful and desirable. FDP also lowered the levels of lactic acid in sickle cell patients. However, it should be noted that measuring lactate levels in homogenized whole blood samples, rather than from isolated red blood cells, will skew this value somewhat.

When blood from healthy people who do not have the disease was analyzed, the results showed that an intravenous infusion of FDP prior to blood sampling caused a small (but statistically significant) increase in median ATP and DHAP levels, and a slight decrease (not statistically significant) in pyruvate levels. FDP also caused a significant drop in lactate levels, in blood from healthy people; as noted above, this reading was from homogenized whole blood, rather than from isolated red cells.

An additional set of similar tests were carried out on blood samples taken from four sickle cell patients, using saline-treated and glucose-treated controls compared against FDP treatment using two different concentrations (5 or 10 mg/mL). The results are as follows:

TABLE 2

EFFECT OF FDP ON RED CELL METABOLITES

| Metabolite | Saline Control | Glucose Control | FDP 5 mg/mL | FDP 10 mg/mL |
|---|---|---|---|---|
| ATP, $\mu$mol/mL | 0.8 ± 0.08 | 0.99 ± 0.12 | 1.76 ± 0.03 | 2.86 ± 0.1 |
| DHAP, $\mu$mol/mL | 0.31 ± 0.01 | 0.17 ± 0.02 | 3.30 ± 0.12 | 3.90 ± 0.29 |
| Pyruvate, mg/dL | 11.6 ± 1.8 | 10.8 ± 0.75 | 11.8 ± 0.9 | 11.1 ± 1.08 |
| Lactate, mg/dL | 91.5 ± 5.8 | 214.8 ± 11 | 110 ± 8.7 | 105 ± 14 |

As in the previous tests, FDP caused an increase in ATP and DHAP levels, in a dose-dependent manner. It had no significant effect on pyruvate, and very little effect on lactate; by contrast, glucose treatment cause lactic acid levels to greatly increase.

Example 2

Ability of FDP to Reduce Sickling of Red Blood Cells

Paired samples (2 mL) of whole blood were taken from sickle cell patients who were not suffering an ischemic crisis at the time. FDP (a 5% aqueous solution, added to the whole blood at levels ranging from 0.5 to 2.5 mg FDP per milliliter of blood) was added to one sample from each pair, and an equivalent amount of dextrose was added to the other sample. Dextrose controls were used, to confirm that the effects were not attributable to dilution, and to confirm that FDP can help support anaerobic metabolism under conditions which do not support the metabolism of glucose itself; this approach avoided the question of whether elevated lactate levels might be inhibiting the phosphofructokinase (PFK) enzyme (see, e.g., Hoffman 1976; Kubler and Spieckerman 1978; Opie 1968).

Some of the paired samples were treated with a 2% sodium bisulfite solution. Sodium bisulfite is a reducing compound which tends to acidify the red cells, thereby promoting crystallization of hemoglobin molecules, thereby triggering a sickling reaction in cells from sickle cell patients. Sodium bisulfite treatment is a common and well-recognized chemical method for inducing sickling in red blood cells from sickle cell patients; it is a known and accepted method of testing candidate anti-sickling drugs, to determine how effectively they can help protect against sickling.

The cells were plated, photomicrographed, and assessed by a hematology technician who was not aware of how each sample had been treated.

In the FDP-treated cells, the hematologist observed very few sickled cells, estimated at less than 1% of the cell populations that were studied.

By contrast, in dextrose-treated cells, there was substantial sickling, estimated by the hematologist at 10 to 25% of the cell populations in the various samples that were analyzed.

These two contrasting results clearly indicate that in this type of in vitro test, FDP can help prevent the sickling of red cells from patients with sickle cell disease, while the other sugar did not help.

In addition to the foregoing tests, some of the blood samples (from sickle cell patients) which had not been treated with sodium bisulfite were divided into paired sample, with one sample receiving FDP treatment, while the other sample was treated with dextrose. The cell samples were then subjected to hypoxia, by incubating them at 37° C. for 25 minutes while $N_2$ gas (devoid of any oxygen) was bubbled through the cell incubation media. Like the sodium bisulfite chemical treatment, this type of direct deprivation of oxygen will promote sickling of the cells. The various different samples were then plated, photomicrographed, and assessed by a hematology technician who was not aware of how each sample had been treated.

The results showed a large and statistically significant difference between FDP-treated samples, and glucose-treated samples. The FDP-treated samples contained very few sickled cells, about 2% to 4% with a mean value of 2.4%. By contrast, the glucose-treated control samples had much higher sickling levels, ranging from 5% to 75% with a mean value of 45%.

Both of these results (from bisulfite treatment, and from direct hypoxia) clearly show that FDP can help substantially reduce sickling activity, in stressed cells from sickle cell patients.

Example 3

Ability of FDP to Help Reverse Sickling Activity that has Already Commenced

Paired samples of cells that had been stressed by direct hypoxia (using nitrogen gas treatment) were reoxygenated, and were plated and prepared for analysis by the hematology technician, who was not aware of how each sample had been treated. FDP-treated samples contained sickled cells only in small numbers, less than 1% of the cell populations. By contrast, the glucose-treated control samples had much higher sickling levels, ranging from 10% to 25%.

These data confirm that FDP can help red blood cells from sickle cell patients (1) resist sickling that is caused by chemical stress, using a standard chemical model for inducing sickling; (2) reduces the proportion of cells that sickle when subjected to direct hypoxia; and (3) helps increase the reversibility of sickling, after the hypoxic stress has ended.

Example 4

Ability of FDP to Reduce Cell Breakage and Potassium Release

Red blood cells that have been subjected to various types of stress (such as temperature changes, to which they are not adapted) will suffer measurable levels of hemolysis (cell rupture and breakage), which leads to the release of the cell contents. Hemolysis levels can be assessed using any of several methods, such as automated cells counters, histological observation of fragments, photometric analysis of free red hemoglobin in solution in a supernatant solution after the cell debris has been removed by centrifugation. In addition, potassium ions ($K^+$) can also be measured; these ions are released when cells break apart and hemolyze, and they are also released during the sickling process, when the cells become dehydrated and compacted.

Samples of blood from sickle cell patients were taken, and divided into pairs. One sample from each pair was treated with FDP, and the other with glucose, as described above. Samples were then refrigerated and stored for four days at 4° C. Potassium ion concentrations and free hemoglobin concentrations were measured in the supernatant liquid.

Potassium ion levels were significantly lower in the FDP-treated samples, than in the glucose-treated samples. In addition, there was no visible hemoglobin in any FDP-treated sample; by contrast, every glucose-treated sample showed substantial levels of visible hemoglobin. The FDP-treated samples were essentially clear liquids, while the glucose-treated samples were consistently dark red.

Example 5

Rheological Studies Showing that FDP Can Promote Flexibility and Deformability of Red Blood Cells FDP was also tested to evaluate its "rheologic effects" (this phrase refers to the flow characteristics of a fluid) on red blood cells from patients with sickle cell anemia. This was done using a technique called "$PO_2$ scan ektacytometry". The term $PO_2$ refers to the partial pressure of oxygen in a fluid. It can be easily measured in fluids such as blood, using automated electrodes; it also can be easily controlled and manipulated during the course of an experiment, by bubbling oxygenated gas up through the cell incubation liquid.

Freshly drawn blood samples from patients with sickle cell anemia were centrifuged to isolated red blood cells, and were washed in isotonic buffered saline solution. These studies were performed only on cells from sickle cell patients, since red blood cells from healthy patients (without sickle cell disease) do not exhibit any comparable rheological changes upon deoxygenation.

The RBC's were incubated for two hours at 37° C., in solutions which contained FDP at either 5 mM or 3 mM concentrations. Some of these tests also used a chemical called BW-12C as a positive control; this compound prevents hemoglobin molecules from polymerizing, thereby strongly inhibiting the sickling of the cells even when they are stressed by hypoxia. Some tests also used a mixture of inosine, pyruvate, and phosphate (IPP) as a negative control; this mixture strongly induces sickling.

In each of the experiments shown, the scan ektacytometry measurements were initiated at a $PO_2$ level less than 10 mm Hg. Once a stable baseline had been established, the oxygen tension in the system was increased gradually, over a period of approximately 10 minutes, to a maximum $PO_2$ of approximately 60 mm Hg. A series of scan ektacytometry measurements were taken as the $PO_2$ levels increased from the starting level (10 mm Hg) to the final level (60 mm Hg).

In each of the rheology experiments, the cells in the oxygen gradient system were suspended in a standard viscous, isotonic $PO_2$ scan ektacytometry saline medium that contained 3.1% polyvinylpyrrolidone (PVP). The final medium was adjusted to a pH of 7.4, and an ionic concentration which provided an osmolality value of 290 mOsm.

The first series of tests recorded $PO_2$ scans of control cells (no FDP treatment), and cells that had been pre-incubated with either 3 mM FDP or 5 mM FDP. After preincubation, the cells were washed and then placed into the tonometer, where they were suspended in the viscous, isotonic, PVP-containing solution. The cell suspension was deoxygenated for 20 minutes, achieving a $PO_2$ level of less than 10 mm Hg, after which the scanning process was initiated. As soon as a baseline point was identified, the oxygen pumping system was turned on, and $PO_2$ level began to gradually increase. The increases in cell deformability that occurred as the hemoglobin in the cells depolymerized, and as the cells gradually unsickled and were restored to their normal shapes, was recorded at a series of intervals, as a function of $PO_2$ levels.

Figure 1B:
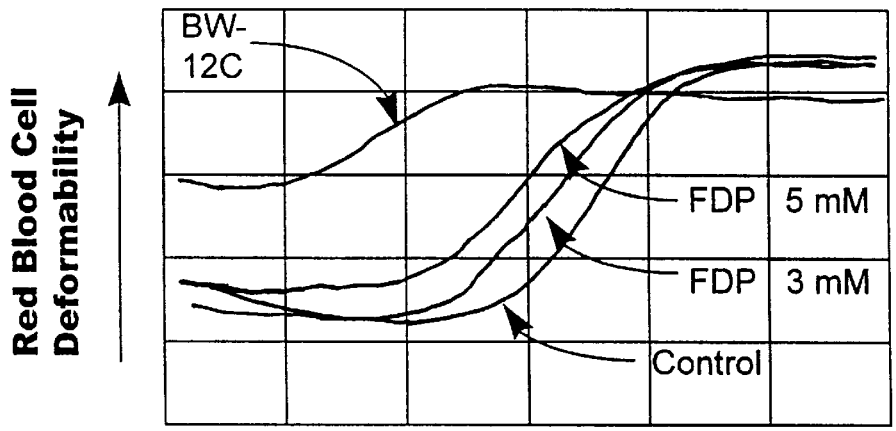
Figure 1C:
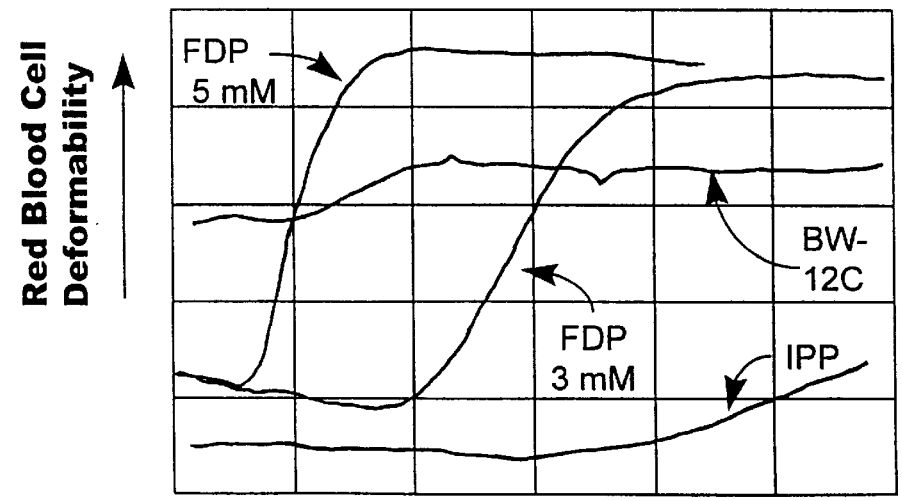

As shown in all three of the graphs in FIG. 1, the results indicated that FDP offered substantial beneficial effects. As depicted in the graphs of FIG. 1A, the displacement of the 5 mM and 3 mM FDP curves, compared to the control curves, can be regarded as either (1) a leftward shift, which indicates earlier and more rapid unsickling, as the cell fluid becomes reoxygenated, or (2) an upward shift, which indicates a higher degree of unsickling at any given oxygen level. This leftward (or upward) shift was dose-dependent; cells treated with 5 mM FDP were shifted farther to the left (or up) than cells treated with 3 mM FDP.

A subsequent test (results shown in FIG. 1B) compared cells that were pre-incubated for two hours with 1 mM BW-12C (which blocks hemoglobin polymerization, thereby blocking sickling, as a positive control) to cells that were incubated with 0, 3, or 5 mM concentrations of FDP. The cells that had been preincubated with FDP were left-shifted (i.e., they unsickled at lower $PO_2$ levels), in a dose-dependent manner, compared to the untreated control cells. Most of the hemoglobin in the cells that were treated with BW-12C never did polymerize, despite the hypoxic treatment.

Still another test (results shown in FIG. 1C) compared cells that were incubated with one of the following: 1 mM BW-12C, as a positive (non-sickling) control; the IPP mixture, as a negative (strongly sickling) control; 5 mM FDP; or nothing at all, as an overall control. In this experiment, treatment with FDP again caused a dose-dependent shift to the left (or upward), compared to untreated controls.

All of these results indicate that FDP can help inhibit or reduce hemoglobin polymerization, and that FDP showed substantial efficacy in increasing and improving the ability of the cells to deform (thereby helping them squeeze through tiny capillaries), despite the stress that was imposed on the cells by low oxygen concentrations.

In summary, the data from all of the in vitro studies described in Examples 1 through 5 support the assertion that FDP can be useful and helpful, in treating patients who are suffering from the recurrent ischemic crises caused by sickle cell anemia.

Example 6

Tests on Human Volunteers

The clinical trials on human patients suffering from sickle cell anemia were carried out at four teaching hospitals in the United States. These trials (including their designs and implementation procedures) were approved by the U.S. Food and Drug Administration, and by an Institutional Review Board at each participating hospital.

In these trials, volunteers were selected from the population of sickle cell patients who arrived at the hospital, suffering from an acute ischemic crisis that was severe enough to require hospitalization. All patients were stabilized using conventional care (with painkillers, antibiotics, etc.) for at least 4 hours before any FDP was infused into them. They were also screened, to determine whether they met both the inclusion and exclusion criteria, discussed above. Those who did, and who chose to participate in the trial, were divided into random groups. Each group receiving 100 mg/kg FDP or less contained 9 patients, (including the placebo group, which received a solution containing 5% dextrose as a control). The group receiving 100 mg/kg FDP contained 10 patients. The various dosage groups (50, 100, or 250 mg/kg) were kept balanced with each other regarding factors such as age, gender, and weight. The treatments were double-blinded; no recipient knew whether FDP was in their infusion fluids, and the hospital personnel who administered the fluids and interacted with the patients also did not know what was in each infusion bag.

After initial stabilization for 4 hours, a blood sample was taken to determine baseline data, and an infusion of FDP or placebo was then given over 30 minutes. Identical volumes (450 mL) were given to all patients, regardless of dosage, which was controlled by varying the concentration of the FDP in the solution. Additional blood samples were taken immediately after the infusion ended, and after 1 and 4 hours. Blood samples were analyzed by smear microscopy and for red cell ATP content.

A baseline (pre-treatment) value for pain intensity was determined for each patient, using both the numerical and -visual (horizontal line) reporting scales described above. The FDP (or placebo) was then intravenously infused into the patient over a period of 30 minutes, and the patient was asked to report pain levels again at 1, 2, 3, 4, 8, 12, 16, and 24 hours after the FDP infusion had begun. Mean values were determined for each treatment group at each time, and these values were compared against the pre-treatment baseline values, to determine pain intensity differential (PID) values.

Consumption of meperidine (a narcotic drug, also known by the trademarked name "Demerol") was also recorded. However, many sickle cell patients exhibit a strong tendency toward "morphine-seeking behavior," attributable largely to a lifelong struggle with a never-ending series of highly painful crises. Accordingly, during a painful ischemic episode, most sickle cell patients will take as much or as many pain relievers as they can obtain. Accordingly, such measurements usually are not a reliable indicator of actual pain relief.

The results of the PID analyses are displayed in FIGS. 2 and 3, each of which contains two related graphs. The top graph in each figure indicates on-going PID values at each reporting period. The bottom graph in each figure indicates the cumulative differential scores (in essence, the area under the curves in the top graphs), which indicates the total amount of time-dependent pain-relieving benefit received by the patients. Each data point in these graphs represents a mean value for all patients in a particular treatment group.

The results shown in these figures clearly indicate that FDP provided significant pain relief, during ischemic episodes.

Thus, there has been shown and described a new and useful method for using fructose-1,6-diphosphate as an analgesic drug, to reduce the pain that is suffered by sickle cell anemia patients during their recurrent ischemic crises.

Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Angelos, M. G., et al, "FDP fails to limit early myocardial infarction size in a canine model," *Ann. Emerg. Med.* 22: 171–177 (1993)

Barnhart, M. I., et al, *Sickle Cell*. Library of Congress card no. 73–92193 (1976)

Cacioli, D., et al, "Haemorheological effects of FDP in patients with lower extremity ischaemia," *Curr Med Res Opin* 10: 668–74 (1988)

Colomer, D., et al, "Erythrocyte fructose 2,6-bisphosphate content in congenital hemolytic anemias," *Hemoglobin* 15: 517–23 (1991)

Crescimanno, M., et al, "Influence of FDP on the lung antioxidant defenses of mice with endotoxemia," *Pharmacol Res* 22: 74–75 (1990)

Dean, J., and Schechter, A. N., "Sickle cell anemia: molecular and cellular bases of therapeutic approaches," *New Eng J Med* 299: 752–763 (Part 1); 804–811 (Part 2); 863–870 (Part 3) (1978)

Eddy, L. J., et al, "Lack of a direct metabolic effect of FDP in ischemic myocardium," *Am J Physiol* 241: H576–83 (1995)

Galzigna, L., et al, "Some effects of FDP on rat myocardial tissue relate to a membrane stabilizing action," *Cell Biochem. Function* 7: 91–96 (1989)

Gobbel, G. T., et al, "Response of cerebral endothelial cells to hypoxia: modification by FDP but not glutamate receptor antagonists," *Brain Res* 653: 23–30 (1994)

Granot, H., et al, "Successful treatment of irreversible hemorrhagic shock in dogs with FDP and dichloroacetate," *Circ Shock* 163–73 (1985)

Gregory, G. A., et al, "FDP reduces ATP loss from hypoxic astrocytes," *Brain Res* 516: 310–2 (1990)

Hardin, C. D., et al, "Metabolism of exogenously applied FDP in hypoxic vascular smooth muscle," *Am J Physiol* 267: H2325–32 (1994)

Hassinen, I. E., et al, "Mechanism of the effect of exogenous FDP on myocardial energy metabolism," *Circulation* 83: 584–93 (1991)

Hoffmann, E., "The significance of phosphofructokinase to the regulation of carbohydrate metabolism," *Rev Physiol Biochem Pharmacol* 75: 2–68 (1976)

Kelleher, J. A., et al, "Energy metabolism in hypoxic astrocytes: protective mechanism of FDP," *Neurochem Res* 20: 785–92 (1995)

Kubler, W. and Spieckermann, P. G., "Regulation of glycolysis in the ischemic and anoxic myocardium," *J Mol Cell Cardiol* 1: 351–377 (1978)

Lazzarino, G., et al, "Ischemia and reperfusion: effect of FDP," *Free Radic Res Commun* 16: 325–39 (1992)

Lazzarino G., et al, "Protective effects of exogenously administered FDP from ischemia reperfusion damage induced on isolated rat heart," *Ital J Biochem* 38: 251A–253A (1989)

Markov, A. K., et al, "Hemodynamic, electrocardiographic, and metabolic effects of FDP on acute myocardial ischemia," Am *Heart J* 100: 639–46 (1980)

Markov, A. K., "Hemodynamics and metabolic effects of FDP in ischemia and shock: Experimental and clinical observations," *Ann Emerg Med* 15: 1470–7 (1986)

Markov, A. K., et al, "Increasing survival of dogs subjected to hemorrhagic shock by administration of FDP," *Surgery* 102: 515–27 (1987)

Myers, J., et al, "Effect of FDP on exercise capacity in patients with peripheral vascular disease," *Int J Sports Med* 11: 259–262 (1990)

Nakai, T., et al, "Beneficial effects of FDP infusion on liver regeneration after ischemic liver injury," *Gastroenterology Japan* 26: 611–8 (1991)

Opie, L. H., "Metabolism of the heart in health and disease," *Am Heart J* 76: 685–698 (1968)

Pasque, M. K., et a, "Metabolic intervention to affect myocardial recovery following ischemia," *Annals of Surgery* 200: 1–12 (1984)

Platt, O. S., et al, "Mortality in sickle cell disease: life expectancy and risk factors for early death," *New Eng J Med* 330: 1639–1644 (1994)

Sano, W., et al, "Beneficial effect of FDP on mitochondrial function during ischemia-reperfusion of rat liver," *Gastroenterology* 108: 1785–92 (1995)

Tortosa, A., et al, "FDP fails to ameliorate delayed neuronal death in the CA1 area after transient forebrain ischaemia in gerbils," *Neuropharmacology* 32: 1367–71 (1992)

What is claimed is:

1. A method for treating a sickle cell anemia patient during an ischemic crisis which involves sickling of red blood cells in the patient, comprising the step of co-administering a drug useful for treating sickle cell crises and fructose-1, 6-diphosphate to a patient who suffers from sickle cell anemia during an ischemic crisis involving sickling of red blood cells in the patient, wherein the fructose-1, 6-diphosphate is administered in a dosage which is therapeutically effective in reducing pain in sickle cell anemia patients during ischemic crises which involve sickling of red blood cells.

2. A method for treating a sickle cell anemia patient during an ischemic crisis which involves sickling of red blood cells in the patient, comprising administering fructose-1, 6-diphosphate to the patient in a dosage which is therapeutically effective in reducing the need for potentially addictive pain killers during ischemic crises which involve sickling of red blood cells.

3. A method of treating a patient suffering from sickle cell anemia comprising administering fructose-1,6-diphosphate in a dosage therapeutically effective to reduce or prevent complications associated with sickle cell anemia.

4. The method of claim 3 wherein the complications associated with sickle anemia are organ and tissue damage in the sickle cell anemia patient.

5. The method of claim 1, 2, or 3, wherein the fructose-1,6-diphosphate is administered to the patient by means of intravenous infusion.

6. The method of claim 1, 2, or 3, wherein the fructose-1,6-diphosphate is administered to the patient at a dosage of at least about 40 milligrams of fructose-1,6-diphosphate per kilogram of patient body weight.

7. The method of claim 4 wherein the fructose-1,6-diphosphate is administered in an amount sufficient to cause an increase in ATP in the sickle cell.

8. The method of claim 4 wherein the fructose-1,6-diphosphate is administered in an amount sufficient to reduce the sickling effect of the red blood cells in the patient.

9. The method of claim 4 wherein the fructose-1,6-diphosphate is administered in an amount sufficient to reduce cell breakage and potassium release in cells that had been subjected to stress in sickle cell patients.

* * * * *